United States Patent [19]

Gerhardt

[11] Patent Number: 4,513,455

[45] Date of Patent: Apr. 30, 1985

[54] VERTICALLY STACKED DOUBLE POCKET

[76] Inventor: Gilbert C. Gerhardt, 225 Great Rd., Maple Shade, N.J. 08052

[21] Appl. No.: 557,625

[22] Filed: Dec. 2, 1983

[51] Int. Cl.³ .......................................... A41D 27/20
[52] U.S. Cl. .......................................... 2/253; 2/246
[58] Field of Search ................... 2/247, 248, 250, 249, 2/252, 251, 253, 94

[56] References Cited

U.S. PATENT DOCUMENTS

| | | | |
|---|---|---|---|
| 874,815 | 12/1907 | Williams | 2/252 |
| 1,257,048 | 2/1918 | Tamas | 2/253 |
| 2,304,235 | 12/1942 | Boots | 2/252 |
| 2,508,190 | 5/1950 | Previdi | 2/253 |
| 3,744,059 | 7/1973 | Hayes | 2/250 |
| 3,968,522 | 7/1976 | Riess | 2/250 |

*Primary Examiner*—Doris L. Troutman
*Attorney, Agent, or Firm*—Paul Maleson

[57] ABSTRACT

A vertically stacked double pocket is provided on tennis shorts or the like. The pocket has an upper and lower section and an elastic band at the top of each section. The pocket is closed at the bottom and sides and open at the top of the upper section. The lower section communicates with the upper section. A tennis ball or the like may be inserted and retained in the lower section and another may be inserted and retained in the upper section.

9 Claims, 5 Drawing Figures

VERTICALLY STACKED DOUBLE POCKET

BACKGROUND OF THE INVENTION

Certain sports or games, of which tennis is the typical example, require that the player have ready access to more than one ball. In tennis, the server quickly serves a second ball if the first is a fault. It is desirable to have a means for having two tennis balls available without hampering the motion of the player and without interrupting his concentration. This invention is directed to solving this problem.

It has been known to provide special pockets for sports balls. Pockets for attachment to tennis shorts have been known, and horizontally disposed multiple pockets are known. Pockets to hold a plurality of balls are known. However, it is not believed that any prior expedient provided a means to store one or two balls with easy access and firm retention, as in the present invention.

A vertically stacked double pocket is provided on tennis shorts or the like. The pocket has an upper section and a lower section. Elastic bands are provided at the top of each section. The pocket is closed at the bottom and the sides and is open at the top. The top of the bottom section is open into the bottom of the top section. The elastic bands tend to close the tops of the respective sections but the bands are easily stretchable and deformable to permit the passage of a ball therethrough.

Preferably, pleats are provided on each section so that when no ball is present, the pocket section tends to lie flat, and when a ball is present, the section expands to accomodate it.

A first ball may be passed through the top of the pocket, past both bands, and be retained securely in the lower section. If desired, a second ball may be inserted in the upper section, and also be held securely. The balls may be withdrawn in order at will. Both balls are inserted and removed at the same place, which is desirable for maintaining the player's concentration. The preferable location of the pocket is at the rear of the garment, to one side of the rear center line. The pocket is simple, inconspicuous, effective and easy to use with a minimum of interruption to the player and retains the balls with a minimum of interference with the player's motion in play.

DESCRIPTION OF THE PREFERRED EMBODIMENT

Figure 1:
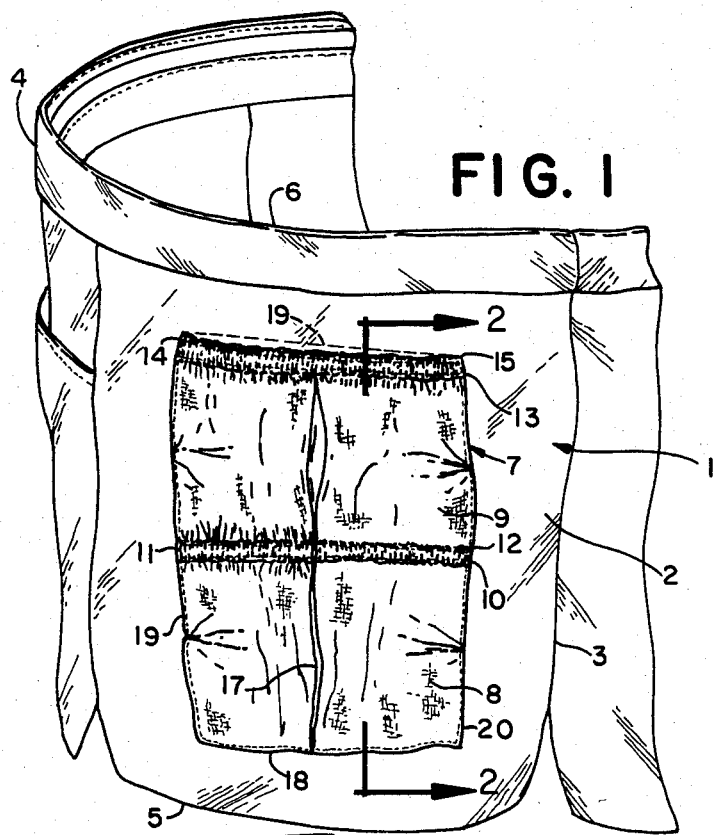
FIG. 1 is a perspective view taken from the left rear, of a pair of tennis shorts, partially fragmented, showing the novel double pocket.

The invention is best initially understood in connection with FIG. 1, which best shows the context. Only the left rear of a pair of tennis shorts is shown, since the invention may be fully described in connection therewith. The shorts are generally designated 1. The shorts 1 have a top edge 6 and a bottom edge 5. They are provided with a conventional waistband 4.

The left rear portion of the shorts, designated 2, are separated from the right rear portion by a seam 3, as is conventional. The vertically stacked double pocket of the invention is generally designated 7.

The pocket 7 comprises a lower section 8 and an upper section 9. Each of the said sections is of dimensions to accomodate a single tennis ball. It will be appreciated that since the two sections are stacked vertically, the combined height of the double pocket is approximately twice that necessary to retain a tennis ball.

The pocket is affixed to the main or basic structure of the shorts at the lower edge thereof 18, the left edge 19, and the right edge 20. A preferred and typical method of affixation is by sewing. The top remains open and unattached. The open top is indicated by the line 19 which parallels the top edge 15 of the pocket and is on the rear of the pants leg.

An important aspect of the invention is the pair of elastic bands provided at the top of each pocket section. The top elastic band 14 has a lower edge 13 and an upper edge 15 which is coincident with the top of the double pocket. The lower elastic band 11 has a top edge 12 and a bottom edge 10. The elastic band structure is in itself conventional. An elongated strip of elasticized fabric is sewn along its upper and lower edges to the inside of the cloth of which the pocket is made.

The elastic strip is slightly stretched as it is sewn, so that after the stitches are inserted, the stop tends to contract along its length. This produces a shirr, that is, a sucession of closely spaced folds which have a gathered appearance. The important characteristic of the shirr is that it has a normal unbiased length which accords with the other lateral dimensions of the pocket, permitting the pocket to lie flat, and a stretched condition in which the elastic is stretched and the small pleats or folds are opened, so that the length is increased. This lengthening permits the insertion and removal of the tennis balls.

Figure 2:
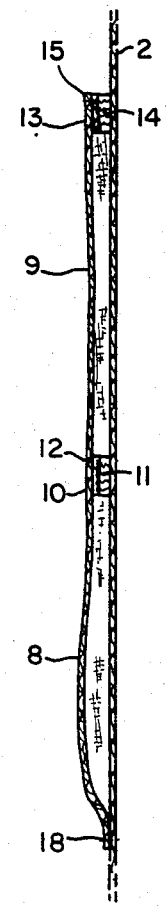
FIG. 2 is a cross-sectional view, partially fragmented, taken on line 2—2 of FIG. 1.

FIG. 2 more clearly shows the structure of the pocket. As shown, a line of conventional stitches defines the bottom edge 18 of the pocket. In FIG. 2, the double pocket is shown empty, and the pocket lies relatively flat against the seat of the pants.

If a ball were inserted into the top of the pocket, the upper band 14 would expand elastically to permit its passage, and would then return to its shortened unbiased length. If the ball is forced further down, the lower band 11 expands in the same way, and if the ball is forced past the lower band 11 into the lower section 8, the lower band 11 returns to to shortened condition.

Figure 3:
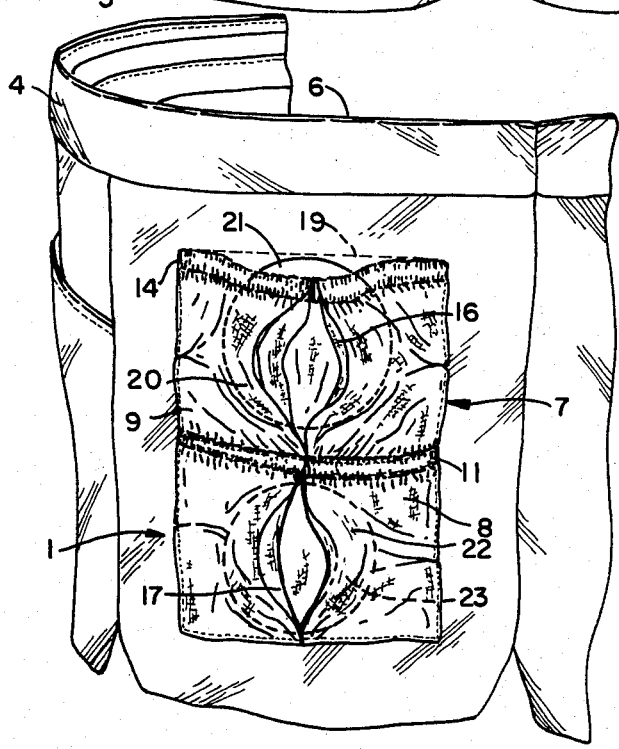
FIG. 3 is an elevation view of the pocket, showing two vertically stacked balls.

FIG. 3 shows the double pocket 7 with a lower ball 23 in the lower pocket section 8. It causes an externally visible bulge 22 in the lower section. FIG. 3 also shows a second ball, an upper ball 21, in the upper section 9. This ball causes an externally visible bulge 20 in the upper section 9. The uppermost portion of the ball 21 is shown visible at the top of the pocket. When fully inserted, the upper ball is almost or completely hidden by the contraction of the upper band 14 to its unbiased state. For more explicit illustration, FIG. 3 shows more of the upper ball 21 then would generally be visible when the ball is fully inserted. Thus, this figure more accurately shows the upper ball in the process of being inserted, when it is almost but not quite all the way in the upper pocket section.

The action of the elastic bands, as has been described, is important to the operation of this invention. The lower band 11 serves to retain the lower ball 23 in the lower section 8, whether there is an upper ball stored or not.

Similarly, the upper band 14 retains the upper ball 21 in the upper section 9. The balls may be easily inserted and removed by hand when desired, but remain firmly and reliably in place otherwise, even during the active motions of play of the sport.

Figure 4:
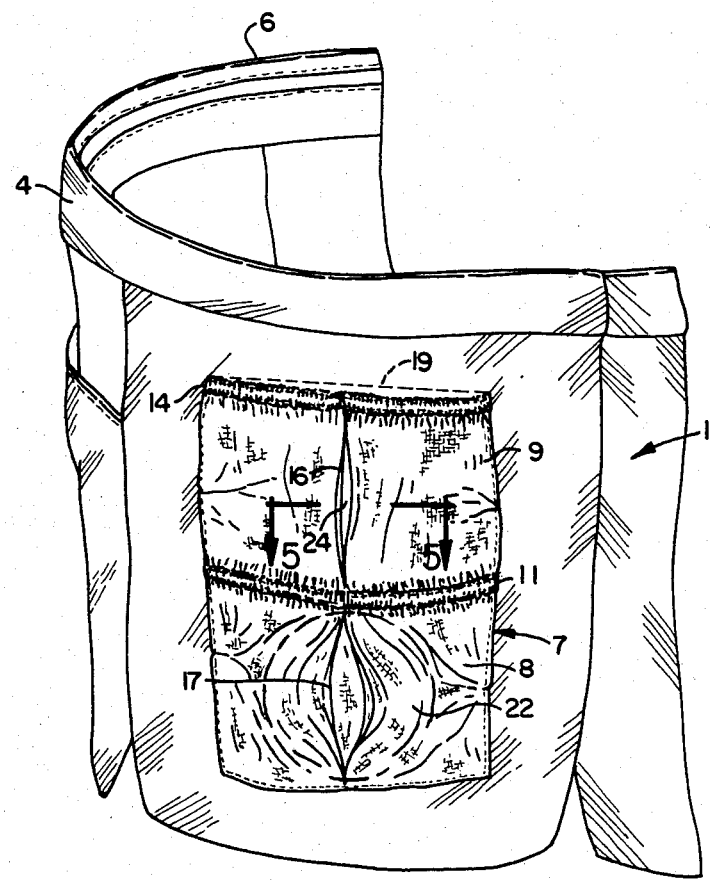
FIG. 4 is an elevation view of the pocket, showing a ball in the lower section only; and, FIG. 5 is a cross-sectional view taken on line 5—5 of FIG. 4, showing a pleat construction.

FIG. 4 is a view of the pocket which is similar in all respects to the pocket as described above in connection with FIG. 3, except that there is only the lower ball 23 in place, whose presence is indicated by the bulge 22.

Both the upper and lower sections of the double pocket are preferably provided with vertical pleats. the pleat in the upper section is designated 16 and the pleat in the lower section is designated 17.

Figure 5:
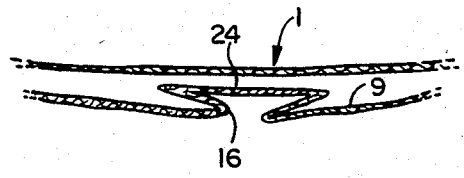

FIG. 5, taken on line 5—5 of FIG. 4, shows the structure of the vertical pleat in more detail. At the pleat 16, the material of the pocket section 9 is folded four times as shown so that an inner pleat surface 24 is formed. The purpose of the pleats is to permit the pocket to lay relatively flat when no ball is retained, and to provide enough cloth material to accomodate a ball without unduly stressing the material of the pocket. Thus, when no ball is present, just a little of the inner pleat 24 shows, and when a ball is present, the edges 16 separate and more of the inner pleat 24 is visible.

It is preferable that the double pocket be positioned at the seat of the shorts at the rear, approximately as shown. This position produces the least interference with the activity of the player. The principle of the vertically stacked double pocket would still apply if the pocket is more to the side of the shorts, but there is more chance of the hand or arm of the player striking it in such position. The concept of the vertical double stack has been found to be an important advantage in the practical use of the shorts. Pockets seperately provided or provided in horizontal spacing produce disadvantages when compared to the present invention. They have more tendency to interfere with the natural motions, particularly the arm motions, of the player.

Furthermore, it has been found to be an important advantage to have the entrance for both balls at the same place, that is, at the top of the upper section. This is a subtle but valuable advantage that may only be appreciated by a player. Typically, one ball may be served, and if the serve is a fault, it is desirable to serve again with a minimum of delay, for well understood reasons. The ability with this invention to reach for the same spot every time, on either the first or second serve, to get a ball, has been found advantageous.

Similarly, the ability with this invention for the player to insert the balls at the same spot without thinking or searching has proved to be an aid to unbroken concentration by the player. The secure retention of either one or two balls as required is also an aid to efficient play.

For right handed players, location on the left rear is preferred as being least likely to interfere with motion. A position on the right rear would be better for left handed players.

The invention has been described in connection with tennis, but it is applicable to the similar family of games and sports in which similar conditions occur, for example, racquet ball.

The vertical pleat has been shown and described as a single central pleat. Such variations as providing a pair of side pleats are within the spirit of the invention. Though less desirable, pleats could be eliminated. Though the preferred location has been shown and described, other locations are within the spirit of the invention. As shown, the pocket is made of a single piece of cloth, cut, folded and sewn to form the entire structure. The elasticized strips are of course separate pieces. This integral construction is preferred. The pocket is shown without a backer, but within the teaching, a backer or a lined pocket could be provided.

The cloth material of the pocket is preferably the same as the material of the main portion of the shorts, but not necessarily so. The invention is most commonly of application to shorts, but the principle applies to skirts as a base as well.

I claim:

1. A vertically stacked double pocket affixed to the exterior of a garment, said pocket comprising a lower section and an upper section, said lower section closed at the bottom and open at the top into the bottom of said upper section, said upper section being open at the top and the bottom thereof, and a lower elastic band at the top of said lower section separating said upper and lower sections and an upper elastic band, said upper band being positioned at the top of said upper section, each said section closed at the top thereof only by said elastic band at the top thereof, each of said upper and lower sections being substantially equal in size and shape and vertically aligned and having the side edges of each section attached to said garment, and each section being dimensioned to receive and retain a ball.

2. A pocket as set forth in claim 1 wherein each of said elastic bands has a normal unbiased condition tending to close the top of its respective pocket.

3. A pocket as set forth in claim 2 wherein each said elastic band has a stretched condition in which the section at whose top said band is positioned is open to permit the passage of a ball, each said band tending to retain a ball below it when said band is in its unbiased condition.

4. A pocket as set forth in claim 3 wherein each of said upper and lower sections is provided with a pleat, said pleat permitting the expansion of the interior of the said section to accomodate a ball therein, and causing said section to tend to lie flat when no ball is retained therein.

5. A pocket as set forth in claim 4 wherein said pocket is affixed to said garment at the rear of said garment.

6. A pocket as set forth in claim 5, wherein said pocket is affixed to said garment to one side of the rear center line of said garment.

7. A pocket as set forth in claim 6 wherein each said section is dimensioned to accomodate and retain a tennis ball, one tennis ball being retained in said lower section and a second tennis ball, if present, being retained in said upper section.

8. A pocket as set forth in claim 7 wherein said garment is a pair of pants.

9. A pocket as set forth in claim 7 wherein said garment is a skirt.

* * * * *